United States Patent [19] [11] Patent Number: 5,948,809
Chiu et al. [45] Date of Patent: *Sep. 7, 1999

[54] (−) CIS-6(S)-PHENYL-5(R)[4-(2-PYRROLIDIN-1-YL ETHOXY) PHENYL]-5,6,7,8-TETRAHYDRONAPHTHALEN-2-OL-D-TARTRATE

[75] Inventors: Charles K. Chiu, Attleboro, Mass.; Morgan Meltz, Niantic, Conn.

[73] Assignee: Pfizer Inc, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/065,094

[22] PCT Filed: Oct. 4, 1996

[86] PCT No.: PCT/IB96/01049

§ 371 Date: Apr. 28, 1998

§ 102(e) Date: Apr. 28, 1998

[87] PCT Pub. No.: WO97/16434

PCT Pub. Date: May 9, 1997

Related U.S. Application Data

[60] Provisional application No. 60/006,125, Nov. 2, 1995.

[51] Int. Cl.[6] ............... A61K 31/40; C07D 207/06; C07D 295/084; C07D 295/088

[52] U.S. Cl. ............... 514/428; 548/575; 548/576; 548/578; 548/579

[58] Field of Search ............... 514/428; 548/575, 548/576, 578, 579

[56] References Cited

U.S. PATENT DOCUMENTS 3,234,090  2/1966  Huebner et al. ............... 167/58
3,277,106  10/1966  Bencze et al. ............... 260/295

FOREIGN PATENT DOCUMENTS 9621656  7/1996  WIPO ............... C07D 295/08

OTHER PUBLICATIONS

J. Med. Chem., pp. 880–885, Daniel Lednicer, et al.: "Mammalian Antifertility Agents. VI. A Novel Sequence for the Preparation of 1,2–Disubstituted 3,4–Dihydronaphthalenes"(1969).

*Primary Examiner*—Johann Richter
*Assistant Examiner*—Jane C. Oswecki
*Attorney, Agent, or Firm*—Peter C. Richardson; Gregg C. Benson; Mervin E. Brokke

[57] ABSTRACT

(−)Cis-6(S)-phenyl-5(R)-[4-(2-pyrrolidin-1-yl ethoxy) phenyl]-5,6,7,8-tetrahydro-naphthalen-2-ol D-tartrate, pharmaceutical compositions comprising this compound, and an advantageous process for preparing the compound.

10 Claims, No Drawings

# (−) CIS-6(S)-PHENYL-5(R)[4-(2-PYRROLIDIN-1-YL ETHOXY) PHENYL]-5,6,7,8-TETRAHYDRONAPHTHALEN-2-OL-D-TARTRATE

This Appln. claims the benefit of U.S. Provisional Appln. Ser. No. 60/006,125, Nov. 2, 1995. This application is a 371 of PCT/IB96/01049 filed Oct. 4, 1996.

BACKGROUND OF THE INVENTION

The present invention relates to (−) cis-6(S)-phenyl-5(R)-[4-(2-pyrrolidin-1-ylethoxy)phenyl]-5,6,7,8-tetrahydronaphthalen-2-ol D-tartrate which is useful as an estrogen agonist, and to a process for its preparation.

The preparation of (−) cis-6(S)-phenyl-5(R)-[4-(2-pyrrolidin-1-ylethoxy)phenyl]-5,6,7,8-tetrahydronaphthalen-2-ol, as its free base and R-binap salt is described in commonly owned U.S. patent application Ser. No. 08/369,954, now U.S. Pat. No. 5,552,412, the text of which is hereby incorporated by reference.

SUMMARY OF THE INVENTION

This invention is directed toward (−) cis-6(S)-phenyl-5(R)-[4-(2-pyrrolidin-1-ylethoxy)phenyl]-5,6,7,8-tetrahydronaphthalen-2-ol D-tartrate.

In another aspect, this invention is directed toward a method of preparation of (−)cis-6(S)-phenyl-5(R)-[4-(2-pyrrolidin-1-ylethoxy)phenyl]-5,6,7,8-tetrahydronaphthalen-2-ol D-tartrate which comprises:

1) dissolving racemic or partially optically enriched cis-6(S)-phenyl-5(R)-[4-(2-pyrrolidin-1-ylethoxy)phenyl]-5,6,7,8-tetrahydronaphthalen-2-ol in boiling aqueous ethanol to form a solution;

2) adding an equal molar amount of D-tartaric acid dissolved in aqueous ethanol to said solution to form a second solution;

3) cooling said second solution; and 4) collecting the product formed in step 3.

In another aspect this invention provides a pharmaceutical composition comprising (−)cis-6(S)-phenyl-5(R)-[4-(2-pyrrolidin-1-ylethoxy)phenyl-]5,6,7,8-tetrahydronaphthalen-2-ol D-tartrate and a pharmaceutically acceptable carrier.

In yet another aspect, this invention provides methods for treating or preventing diseases or conditions which are susceptible to treatment or prevention by estrogen agonists which comprises administering to a mammal in need of such treatment or prevention an effective amount of (−)cis-6(S)-phenyl-5(R)-[4-(2-pyrrolidin-1-ylethoxy)phenyl]-5,6,7,8-tetrahydronaphthalen-2-ol D-tartrate.

DETAILED DESCRIPTION OF THE INVENTION

Racemic cis-6-phenyl-5-[4-(2-pyrrolidin-1-ylethoxy) phenyl]-5,6,7,8-tetrahydronaphthalen-2-ol contains two asymmetric carbons corresponding to two optically active compounds. Resolution of this racemate has been previously accomplished by crystallization of the salt with R-(−)-1,1'binaphthyl-2,2'-diyl hydrogen phosphate (R-binap) as described in commonly owned U.S. application Ser. No. 08/369,954, now U.S. Pat. No. 5,552,412. Since R-binap is not a suitable salt for pharmaceutical use, the R-binap product must be further converted to the free base and finally to a pharmaceutically acceptable salt.

D-tartaric acid has been found to form a 1:1 salt with racemic or partially optically enriched cis-6-phenyl-5-[4-(2-pyrrolidin-1-ylethoxy)phenyl]-5,6,7,8-tetrahydronaphthalen-2-ol in aqueous ethanol.

Upon cooling, the desired (−) isomer separates as a solid and is easily collected, thus providing a pharmaceutically acceptable salt of the (−) cis isomer in high yield and purity in a single reaction step. Aqueous ethanol is the preferred solvent for this procedure; 95% aqueous ethanol is the preferred mixture.

This invention is readily carried out by dissolving racemic or partially optically enriched cis-6-phenyl-5-[4-(2-pyrrolidin-1-ylethoxy)phenyl]-5,6,7,8-tetrahydronaphthalen-2-ol with an equal molar amount of D-tartaric acid in boiling aqueous ethanol; 95% ethanol is preferred. The amount of solvent must be adequate to effect complete solution of the salt. This has been found to be about 10 to 15 mL per gram of racemic compound.

Upon cooling to room temperature, the desired (−) cis isomer separates as a solid. This product has an optical purity of about 95%. Washing with 95% ethanol under reflux produces a product with greater than 99% optical purity.

The compound of this invention is a valuable estrogen agonist and is useful for oral contraception; relief for the symptoms of menopause; prevention of threatened or habitual abortion; relief of dysmenorrhea; relief of dysfunctional uterine bleeding; relief of endometriosis; an aid in ovarian development; treatment of acne; diminution of excessive growth of body hair in women (hirsutism); the prevention and treatment of cardiovascular disease; prevention and treatment of atherosclerosis; prevention and treatment of osteoporosis; treatment of benign prostatic hyperplasia and prostatic carcinoma obesity; and suppression of post-partum lactation. This compound also has a beneficial effect on plasma lipid levels and as such are useful in treating and preventing hypercholesterolemia.

While the compound of this invention is an estrogen agonist in bone, it is an antiestrogen in breast tissue and as such would be useful in the treatment and prevention of breast cancer.

Control and Prevention of Endometriosis

The protocol for surgically inducing endometriosis is identical to that described by Jones, Acta Endoerinol (Copenh) 106:282–8. Adult Charles River Sprague-Dawley CD® female rats (200–240 g) are used. An oblique ventral incision is made through the skin and musculature of the body wall. A segment of the right uterine horn is excised, the myometrium is separated from the endometrium, and the segment is cut longitudinally. A 5×5 mm section of the endometrium, with the epithelial lining apposed to the body wall, is sutured at its four corners to the muscle using polyester braid (Ethiflex, 7-0®). The criterion of a viable graft is the accumulation of fluid similar to that which occurs in the uterus as a result of oestrogen stimulation.

Three weeks after transplantation of the endometrial tissue (+3 weeks) the animals are laparotomized, the volume of the explant (length×width×height) in mm was measured with calipers, and treatment is begun. The animals are injected sc for 3 weeks with 10 to 1000 mg/kg/day of the compound of this invention. Animals bearing endometrial explants are injected sc with 0.1 ml/day of corn oil for 3 weeks served as controls. At the end of 3 week treatment period (+6 weeks), the animals are laparotomized and the volume of the explant determined. Eight weeks after cessation of treatment (+14 weeks) the animals are sacrificed; the explant are measured again. Statistical analysis of the explant volume is by an analysis of variance.

Effect on Prostate Weight

Male Sprague-Dawley rats, three months of age are administered by subcutaneous injection of either vehicle (10% ethanol in water), estradiol (30 µg/kg), testosterone (1 mg/kg) or the compound of this invention daily for 14 days (n=6/group). After 14 days the animals are sacrificed, the prostate is removed and the wet prostate weight is determined. Mean weight is determined and statistical significance ($p<0.05$) is determined compared to the vehicle-treated group using Student's t-test.

The compound of this invention decreases prostate weight compared to vehicle. Testosterone has no effect while estrogen at 30 µg/kg reduces prostate weight.

Bone Mineral Density

Bone mineral density, a measure of bone mineral content, accounts for greater than 80% of a bone's strength. Loss of bone mineral density with age and/or disease reduces a bone's strength and renders it more prone to fracture. Bone mineral content is accurately measured in people and animals by dual x-ray absorptiometry (DEXA) such that changes as little as 1% can be quantified. We have utilized DEXA to evaluate changes in bone mineral density due to estrogen deficiency following ovariectomy (surgical removal of ovaries) and treatment with vehicle, estradiol (E2), keoxifen (raloxifen), or other estrogen agonists. The purpose of these studies is to evaluate the ability of the compounds of this invention to prevent estrogen deficiency bone loss as measured by DEXA.

Female (S-D) rats 4–6 months of age undergo bilateral ovariectomy or sham surgery and allowed to recover from anesthesia. Rats are treated by s.c. injection or oral gavage with various doses (10–1000 µg/kg/day, for example) of the compound this invention daily for 28 days. All compounds are weighed and dissolved in 10% ethanol in sterile saline. After 28 days the rats are killed and femora removed and defleshed. The femoral are positioned on a Hologic QDR1000W (Hologic, Inc. Waltham, Mass.) and bone mineral density is determined in the distal portion of the femur at a site from 1 cm to 2 cm from the distal end of the femur using the high resolution software supplied by Hologic. Bone mineral density is determined by dividing the bone mineral content by the bone area of the distal femur. Each group contains at least 6 animals. Mean bone mineral density is obtained for each animal and statistical differences ($p<0.95$) from the vehicle-treated ovariectomy and sham-operated group were determined by t test.

In vitro Estrogen Receptor Binding Assay

An in vitro estrogen receptor binding assay, which measures the ability of the compounds of the present invention to displace [3H]-estradiol from human estrogen receptor obtained by recombinant methods in yeast, is used to determine the estrogen receptor binding affinity of the compound of this invention. The materials used in this assay are: (1) Assay buffer, TD-0.3 (containing 10 nM Tris, pH 7.6, 0.3 M potassium chloride and 5 mM DTT, pH 7.6); (2) The radioligand used is [3H]-estradiol obtained from New England Nuclear; (3) the cold ligand used is estradiol obtained from Sigma (4) recombinant human estrogen receptor, hER.

A solution of the compound is prepared in TD-0.3 with 4% DMSO and 16% ethanol. The tritiated estradiol is dissolved in TD-0.3 such that the final concentration in the assay was 5 nM. The hER is also diluted with TD-0.3 such that 4–10 µg of total protein was in each assay well. Using microtitre plates, each incubate received 50 ul of cold estradiol (nonspecific binding) or the compound solution, 20 uL of the tritiated estradiol and 30 ul of hER solutions. Each plate contains in triplicate total binding and varying concentrations of the compound. The plates are incubated overnight at 4° C. The binding reaction is then terminated by the addition and mixing of 100 mL of 3% hydroxylapatite in 10 mM tris, pH 7.6 and incubation for 15 minutes at 40° C. The mixtures is centrifuged and the pellet washed four times with 1% Triton-X 100 in 10 mM Tris, pH 7.6. The hydroxylapatite pellets are suspended in Ecoscint A and radioactivity is assessed using beta scintigraphy. The mean of all triplicate data points (counts per minute, cpm's) is determined. Specific binding is calculated by subtracting nonspecific cpm's (defined as counts that remain following separation of reaction mixture containing recombinant receptor, radioligand, and excess unlabeled ligand) from total bound cpm's (defined as counts that remain following the separation of reaction mixture containing only recombinant receptor, radioligand). Compound potency is determined by means of IC50 determinations (the concentration of a compound needed to inhibition 50% of the of the total specific tritiated estradiol bound). Specific binding in the presence of varying concentrations of compound is determined and calculated as percent specific binding of total specific radioligand bound. Data are plotted as percent inhibition by compound (linear scale) versus compound concentration (log scale).

Effect on Total Cholesterol Levels

The effect of the compound of the present invention on plasma levels of total cholesterol is measured in the following way. Blood samples are collected via cardiac puncture from anesthetized female (S-D) rats 4–6 months of age that are bilaterally ovariectomized and treated with the compound (10–1000 µg/kg/day, for example, sc or orally for 28 days or with vehicle for the same time), or sham operated. The blood is placed in a tube containing 30 µL of 5% EDTA (10 µL EDTA/1 mL of blood). After centrifugation at 2500 rpm for 10 minutes at 20° C. the plasma is removed and stored at −20° C. unit assay. The total cholesterol is assayed using a standard enzymatic determination kit from Sigma Diagnostics (Procedure No. 352).

Effect on Obesity

Sprague-Dawley female rats at 10 months of age, weighing approximately 450 grams, are sham-operated (sham) or ovariectomized (OVX) and treated orally with vehicle, 17a ethynyl estradiol at 30 mg/kg/day or the compound of this invention at 10–1000 mg/kg/day for 8 weeks. There are 6 to 7 rats in each sub group. On the last day of the study, body composition of all rats is determined using dual energy x-ray abosorptiometry (Hologic QDR-1000/W) equipped with whole body scan software which shows the proportions of fat body mass and lean body mass.

A decrease in fat body mass indicates that the compound of this invention is useful in preventing and treating obesity.

The remedies for prostatic diseases, breast cancer, obesity, cardiovascular disease, hypercholesterolemia and osteoporosis containing the compound of this invention may be administered to animals including humans orally or parenterally in the conventional form of preparations, such as capsules, microcapsules, tablets, granules, powder, troches, pills, suppositories, injections, suspensions and syrups.

The remedies for prostatic diseases, breast cancer, obesity, cardiovascular disease, hypercholesterolemia and osteoporosis containing the compound of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 0.1 mg to 50 mg in unit dosage for both oral and parenteral administration.

The active ingredient may be usually administered once to four times a day with a unit dosage of 0.1 mg to 50 mg in human patients, but the above dosage may be properly varied depending on the age, body weight and medical condition of the patient and the type of administration. A preferred dose is 0.25 mg to 25 mg in human patients. One dose per day is preferred.

The term "treating" as used herein includes preventative (e.g. prophylactic) and palliative treatment.

PREPARATION I

Racemic cis-6-phenyl-5-[4-(2-pyrrolidin-1-yl ethoxy)phenyl]-5,6,7,8-tetrahydronaphthalen-2-ol Step A cis-1-{2-[4-(6-Methoxy-2-phenyl-1,2,3,4-tetrahydronaphthalen-1-yl)phenoxy]ethyl}pyrrolidine. A solution of 1-{2-[4-(6-methoxy-2-phenyl-3,4-dihydronaphthalen-1-yl)phenoxy]ethyl}pyrrolidine hydrochloride (nafoxidene hydrochloride) (1.0 g, 2.16 mmol) in 20 mL of absolute ethanol containing 1.0 g of palladium hydroxide on carbon was hydrogenated at 50 psi at 20° C. for 19 hours. Filtration and evaporation provided 863 mg (93%) of cis-1-{2-[4-(6-methoxy-2-phenyl-1,2,3,4-tetrahydronaphthalen-1-yl)phenoxy]ethyl}pyrrolidine: $^1$H-NMR (CDCl$_3$): d 3.50–3.80 (m, 3H), 3.85 (s, 3H), 4.20–4.40 (m, 3H), 6.80–7.00 (m, 3H); MS 428 (P$^+$+1).

Step B

To a solution of 400 mg (0.94 mmol) of the product from Step A in 25 ml of methylene chloride at 0° C. was added, dropwise with stirring, 4.7 ml (4.7 mmol) of a 1.0 M solution of boron tribromide in methylene chloride. After 3 hours at room temperature, the reaction was poured into 100 ml of rapidly stirring saturated aqueous sodium bicarbonate. The organic layer was separated, dried over sodium sulfate, filtered, and concentrated to afford 287 mg (74% yield) of the title substance as the free base. $^1$H-NMR (CDCl$_3$): d 3.35 (dd, 1H), 4.00 (t, 2H), 4.21 (d, 1H), 6.35 (ABq, 4H). The corresponding hydrochloride salt was prepared by treating a solution of the base with excess 4N HCl in dioxane, followed by evaporation to dryness and ether trituration (MS: 415 [P$^+$+1]).

An alternative method useful for Preparation 1 is described below.

Step A

1-{2-[4-(6-Methoxy-3,4-dihydronaphthalen-1-yl) phenoxy]ethyl}pyrrolidine: A mixture of anhydrous CeCl$_3$ (138 g, 560 mmol) and THF (500 mL) was vigorously stirred for 2 h. In a separate flask, a solution of 1-[2-(4-bromophenoxy)ethyl]pyrrolidine (100 g, 370 mmol) in THF (1000 mL) was cooled to −78° C. and n-BuLi (2.6 M in hexanes, 169 mL, 440 mmol) was slowly added over 20 min. After 15 min, the solution was added to the CeCl$_3$ slurry cooled at −78° C. via cannula and the reaction was stirred for 2 h at −78° C. A solution of 6-methoxy-1-tetralone (65.2 g, 370 mmol) in THF (1000 mL) at −78° C. was added to the arylcerium reagent via cannula. The reaction was allowed to warm slowly to room temperature and was stirred for a total of 16 h. The mixture was filtered through a pad of celite. The filtrate was concentrated in vacuo and 3 N HCl (500 mL) and Et$_2$O (500 mL) were added. After stirring for 15 min, the layers were separated. The aqueous layer was further washed with Et$_2$O (2×). The combined organic layers were dried (MgSO$_4$), filtered, and concentrated to provide 6-methoxy-1-tetralone (22 g). The aqueous layer was basified to pH 12 with 5 N NaOH and 15% aqueous (NH$_4$)$_2$CO$_3$ (1000 mL) was added. The aqueous mixture was extracted with CH$_2$Cl$_2$ (2×). The organic solution was dried (MgSO$_4$), filtered, and concentrated to provide a brown oil. Impurities were distilled off (110–140° C. @ 0.2 mmHg) to yield the product (74 g, 57%). $^1$H NMR (250 MHz, CDCl$_3$): d 7.27 (d, J=8.7 Hz, 2H), 6.92–6.99 (m, 3H), 6.78 (d, J=2.6 Hz, 1H), 6.65 (dd, J=8.6, 2.6 Hz, 1H), 5.92 (t, J=4.7 Hz, 1H), 4.15 (t, J=6.0 Hz, 2H), 3.80 (s, 3H), 2.94 (t, J=6.0 Hz, 2H), 2.81 (t, J=7.6 Hz, 2H), 2.66 (m, 2H), 2.37 (m, 2H), 1.84 (m, 4H).

Step B

1-{2-[4-(2-Bromo-6-methoxy-3,4-dihydronaphthalen-1-yl)phenoxy]ethyl}pyrrolidine: Pyridinium bromide perbromide (21.22 g, 60.55 mmol) was added portionwise to a solution of 1-{2-[4-(6-methoxy-3,4-dihydronaphthalen-1-yl)phenoxy]ethyl}pyrrolidine (23 g, 72 mmol) in THF (700 mL). The reaction was stirred for 60 h. The precipitate was filtered through a Celite pad with the aid of THF. The off-white solid was dissolved in CH$_2$Cl$_2$ and MeOH and was filtered away from the Celite. The organic solution was washed with 0.5 N aq HCl followed by satd NaHCO$_3$ (aq). The organic solution was dried (MgSO$_4$), filtered, and concentrated to provide a brown solid (21.5 g, 83%). $^1$H NMR (250 MHz, CDCl$_3$): d 7.14 (d, J=8.7 Hz, 2H), 6.97 (d, J=8.8 Hz, 2H), 6.71 (d, J=2.2 Hz, 1H), 6.55 (m, 2H), 4.17 (t, J=6.0 Hz, 2H), 3.77 (s, 3H), 2.96 (m, 4H), 2.66 (m, 4H), 1.85 (m, 4H).

Step C

1-{2-[4-(6-Methoxy-2-phenyl-3,4-dihydronaphthalen-1-yl)phenoxy]ethyl}pyrrolidine hydrochloride (Nafoxidene hydrochloride): To a mixture of 1-{2-[4-(2-bromo-6-methoxy-3,4-dihydronaphthalen-1-yl)phenoxy] ethyl}pyrrolidine (19 g, 44 mmol), phenylboronic acid (7.0 g, 57 mmol), and tetrakis(triphenylphosphonium)palladium (1.75 g, 1.51 mmol) in THF (300 mL) was added Na$_2$CO$_3$ (13 g, 123 mmol) in H$_2$O (100 mL). The reaction was heated at reflux for 18 h. The layers were separated and the organic layer was washed with H$_2$O followed by brine. The organic solution was dried (MgSO$_4$), filtered, and concentrated to yield 17.96 g of a brown solid. The residue was dissolved in a 1:1 mixture of CH$_2$Cl$_2$ and EtOAc (250 mL) and 1 N HCl in Et$_2$O (100 mL) was added. After stirring for 2 h, product was allowed to crystallize from solution and 11 g of material was collected by filtration. Concentration of the mother liquor to half its volume provided an additional 7.3 g of product.

Step D cis-1-{2-[4-(6-Methoxy-2-phenyl-1,2,3,4-tetrahydronaphthalen-1-yl)phenoxy]ethyl}pyrrolidine: 1-{2-[4-(6-Methoxy-2-phenyl-3,4-dihydronaphthalen-1-yl)phenoxy]ethyl}pyrrolidine hydrochloride (nafoxidene hydrochloride) (75 g, 162 mmol) was dissolved in 1000 mL of EtOH and 300 mL of MeOH. Dry Pd(OH)$_2$ on carbon was added and the mixture was hydrogenated on a Parr shaker at 50° C. and 50 psi for 68 h. The catalyst was filtered off with the aid of celite and the solvents were removed in vacuo. The resulting white solid was dissolved in CH$_2$Cl$_2$ and the solution was washed with satd NaHCO$_3$ (aq). The organic solution was dried (MgSO$_4$), filtered, and concentrated to yield an off-white solid (62.6 g, 90%).

Step E cis-6-Phenyl-5-[4-(2-pyrrolidin-1-ylethoxy)phenyl]-5,6,7,8-tetrahydronaphthalen-2-ol: A mixture of cis-1-{2-[4-(6-methoxy-2-phenyl-1,2,3,4-tetrahydronaphthalen-1-yl)phenoxy]ethyl}pyrrolidine (12 g, 28 mmol), acetic acid (75 mL), and 48% HBr (75 mL) was heated at 100° C. for 15 h. The solution was cooled and the resulting white precipitate was collected by filtration. The hydrobromide salt (9.6 g, 69%) was dissolved in CHCl$_3$/MeOH and was stirred with satd NaHCO$_3$ (aq). The layers were separated and the aqueous layer was further extracted with CHCl$_3$/MeOH. The combined organic layers were dried (MgSO$_4$), filtered, and concentrated to yield product as an off-white foam. $^1$H NMR (250 MHz, CDCl$_3$): d 7.04 (m, 3H), 6.74 (m, 2H), 6.63 (d, J=8.3 Hz, 2H), 6.50 (m, 3H), 6.28 (d, J=8.6 Hz, 2H), 4.14 (d, J=4.9 Hz, 1H), 3.94 (t, J=5.3 Hz, 2H), 3.24 (dd, J=12.5, 4.1 Hz, 1H), 2.95 (m, 4H), 2.78 (m, 4H), 2.14 (m, 1H), 1.88 (m, 4H), 1.68 (m, 1H).

EXAMPLE 1

(-)Cis-6(S)-Phenyl-5(R)-[4-(2-pyrrolidin-1-yl-ethoxy)phenyl]-5, 6, 7, 8-tetrahydronaphthalen-2-ol D-Tartrate

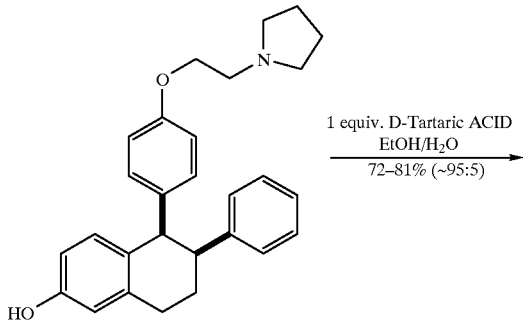

1 equiv. D-Tartaric ACID
EtOH/H$_2$O
72–81% (~95:5)

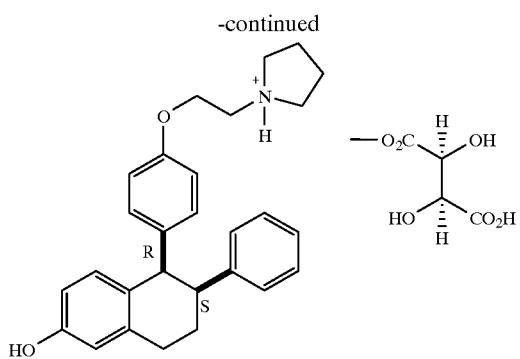

The racemic amine of Preparation 1 (5 g, 12.1 mmol) in a 95:5 mixture of absolute ethanol/water (50 mL) was treated with a solution of D-tartaric acid (1.83 g, 12.1 mmol) in 95:5 mixture of absolute ethanol/water (20 mL). The mixture was heated under gentle reflux and resulted in a homogeneous solution. After heating for 10 minutes, the mixture was allowed to cool and stir at ambient temperature (~25° C.) overnight. The salt precipitated out as a white solids, and was collected by suction filtration, washed with absolute ethanol (20 mL) and sucked dry. The collected white solids (3.75 g) were dried further under house vacuum at room temperature (~25° C.) to yield 2.77 g (81% of theory). Chiral HPLC assay of the salt indicated an optical purity of 95:5 in favor of the desired enantiomer.

The white solids (2.77 g) were suspended in a 95:5 mixture of absolute ethanol/water (28 mL), heated under reflux with stirring for 3.5 hours. After cooling to room temperature, the mixture was granulated overnight. The white solids were collected by suction filtration, washed with ethanol (15 mL) and sucked dry. After drying under house vacuum at room temperature, 2.48 g (95% of theoretical yield) of the resolved salt was obtained with an optical purity of >99:1 as judged by chiral HPLC assay.

We claim:

1. The compound (-)-cis-6(S)-phenyl-5(R)-[4-(2-pyrrolidin-1-ylethoxy)phenyl]-5,6,7,8-tetrahydronaphthalen-2-ol D-tartrate.

2. A pharmaceutical composition comprising (-)cis-6(S)-phenyl-5(R)-[4-(2-pyrrolidin-1-ylethoxy)phenyl-5,6,7,8-tetrahydronaphthalen-2-ol D-tartrate and a pharmaceutically acceptable carrier.

3. A method of preparation for the compound (-) cis-6 (S)-phenyl-5(R)-[4-(2-pyrrolidin-1-yl ethoxy) phenyl]-5,6,7,8-tetrahydronaphthalen-2-ol D-tartrate which comprises:

a) dissolving racemic or partially optically enriched cis-6-phenyl-5-[4-(2-pyrrolidin-1-yl ethoxy)phenyl]-5,6,7,8-tetrahydronaphthalen-2-ol in boiling aqueous ethanol to form a solution;

b) adding an equal molar amount of D-tartaric acid dissolved in aqueous ethanol to said solution to form a second solution;

c) cooling said second solution; and d) collecting the product formed in step C.

4. A method of treating osteoporosis in a mammal which comprises administering to a mammal in need of such treatment an effective amount of the compound of claim 1.

5. A method of treating cardiovascular disease or hyperlipidemia in a mammal which comprises administering to a mammal in need of such treatment an effective amount of the compound of claim 1.

6. A method of treating prostatic disease in a mammal which comprises administering to a mammal in need of such treatment an effective amount of the compound of claim 1.

7. A method of lowering serum cholesterol levels in a mammal which comprises administering to a mammal in need of such treatment an effective amount of the compound of formula I.

8. A method of treating obesity in a mammal which comprises administering to a mammal in need of such treatment an effective amount of the compound of claim 1.

9. A method of treating breast cancer in a mammal which comprises administering to a mammal in need of such treatment an effective amount of the compound of claim 1.

10. A method of treating endometriosis in a mammal which comprises administering to a mammal in need of such treatment an effective amount of the compound of claim 1.

* * * * *